US00RE37536E

(19) United States
(12) Reissued Patent
Barnes

(10) Patent Number: US RE37,536 E
(45) Date of Reissued Patent: Feb. 5, 2002

(54) SPLIT ENERGY LEVEL RADIATION DETECTION

(75) Inventor: Gary T. Barnes, Birmingham, AL (US)

(73) Assignee: UAB Research Foundation

(21) Appl. No.: 08/811,787

(22) Filed: Mar. 4, 1997

Related U.S. Patent Documents

Reissue of:
(64) Patent No.: 4,626,688
Issued: Dec. 2, 1986
Appl. No.: 06/444,605
Filed: Nov. 26, 1982

(51) Int. Cl.[7] ..... G01T 1/20
(52) U.S. Cl. ..... 250/361 R; 250/363.02; 250/367; 250/486.1
(58) Field of Search ..... 250/361 R, 362, 250/363.02, 366, 367, 369, 370.09, 486.1; 378/4, 5, 11, 19, 156

(56) References Cited

U.S. PATENT DOCUMENTS

| | | | |
|---|---|---|---|
| 1,624,443 A | 4/1927 | St John | |
| 2,445,305 A | 7/1948 | Hochgesang | |
| 2,541,599 A | 2/1951 | Morrison | |

(List continued on next page.)

FOREIGN PATENT DOCUMENTS

| | | | | |
|---|---|---|---|---|
| DE | 24 57 853 | | 6/1974 | |
| EP | 0 089 665 | | 3/1983 | |
| EP | 0077018 | * | 4/1983 | ..... 250/370.11 |
| EP | 0 115 125 | | 8/1984 | |
| FR | 2468999 | * | 5/1981 | ..... 250/370.11 |
| GB | 1154973 | | 1/1967 | |
| GB | 2 005 405 A | | 4/1979 | |
| GB | 2 058 511 A | | 4/1981 | |
| JP | 52-2777 | | 10/1977 | |
| JP | A-59 200983 | | 4/1984 | |
| JP | 0200983 | * | 11/1984 | ..... 250/370.11 |
| NL | 7703994 | | 4/1977 | |
| WO | PCT/US80/01015 | | 8/1980 | |

OTHER PUBLICATIONS

L. Brixner and H.Y. Chen, "On the Structural and Luminescent Properties of the $M'LnTaO_4$ Rare Earth Tantalstes, "Journal of the Electrochemical Soc., vol. 130, No. 12 (Dec. 1983) pp. 2435–2443.

L. Brixner, R.S. Holland, R.E. Kellogg, D. Miekish, S.H. Putten and W. Gegarski, "Low Print—Through Technology With Rare Earth Tantalate Phospors." No Date.

(List continued on next page.)

*Primary Examiner*—Georgia Epps
*Assistant Examiner*—Richard Hanig
(74) *Attorney, Agent, or Firm*—Foley & Lardner

(57) ABSTRACT

An energy discriminating apparatus and method is disclosed for use in connection with digital radiography and fluoroscopy. In use of the detection system and method an x-ray source is actuated to direct x-rays through a patient's body, the x-rays including both higher and lower energy radiation. A first detector element, including a plurality of segments, is positioned opposite the source to receive and respond predominantly to x-rays in a lower energy range, the remaining x-rays, being generally of higher energy, passing through the first detector element. A second detector element, also including a plurality of segments, each segment including a phosphor coating layer and a sensor, is positioned to receive and respond to the higher energy radiation passing through the first element. The sensors are coupled respectively to each detector element segment for substantially simultaneously sensing the response and spatial location, relative to the detector elements, of radiation to which each detector element respectively responds. A filter element is interposed between the first and second detectors to enhance discrimination in the energy response of the respective detector elements. Particular preferred detector phosphor materials are identified. The sensors produce separately and simultaneously information representing patterns of relatively lower and higher energy emergent from the patient's body. Digital data processing and conversion equipment responds to the sensors to produce digital information representing each of said images, which can be digitally processed to enhance image characteristics.

35 Claims, 3 Drawing Sheets

U.S. PATENT DOCUMENTS

| | | | |
|---|---|---|---|
| 3,247,377 | A | 4/1966 | Hall, Jr. |
| 3,267,283 | A | 8/1966 | Kapany |
| 3,399,302 | A | 8/1968 | Carrell |
| 3,535,660 | A | 10/1970 | Freedman |
| 3,582,651 | A | 6/1971 | Siedband |
| 3,699,340 | A | 10/1972 | Hick et al. |
| 3,725,704 | A | 4/1973 | Buchanan et al. |
| 3,790,799 | A | 2/1974 | Stein et al. |
| 3,801,785 | A | 4/1974 | Barrett |
| 3,848,130 | A | 11/1974 | Macovski |
| 3,854,049 | A | 12/1974 | Mistretta et al. |
| 3,859,527 | A | 1/1975 | Luckey |
| 3,860,817 | A | 1/1975 | Carmean |
| 3,872,309 | A | 3/1975 | De Belder et al. |
| 3,894,181 | A | 7/1975 | Mistretta et al. |
| 3,925,678 | A | 12/1975 | Eberspaecher et al. |
| 3,936,638 | A | 2/1976 | Gibbons |
| 3,965,358 | A | 6/1976 | Macovski |
| 3,974,386 | A | 8/1976 | Mistretta et al. |
| 4,008,400 | A | 2/1977 | Brunnett et al. |
| 4,029,963 | A | 6/1977 | Alvarez et al. |
| 4,031,401 | A | 6/1977 | Jacob |
| 4,037,104 | A | 7/1977 | Allport |
| 4,047,029 | A | 9/1977 | Allport |
| 4,047,037 | A | 9/1977 | Schlosser et al. |
| 4,055,765 | A | 10/1977 | Gerber et al. |
| 4,055,766 | A | 10/1977 | Miller et al. |
| 4,176,280 | A | 11/1979 | Greschat et al. |
| 4,179,100 | A | 12/1979 | Sashin et al. |
| 4,187,427 | A | 2/1980 | Casano |
| 4,204,225 | A | 5/1980 | Mistretta |
| 4,204,226 | A | 5/1980 | Mistretta et al. |
| 4,217,498 | A | 8/1980 | Racz et al. |
| 4,217,641 | A | 8/1980 | Naparstek |
| 4,225,789 | A | 9/1980 | Albrecht |
| 4,234,792 | A | 11/1980 | DeCou et al. |
| 4,242,583 | A | 12/1980 | Annis et al. |
| 4,247,774 | A | 1/1981 | Brooks |
| 4,255,666 | A | 3/1981 | Wang et al. |
| 4,258,264 | A | 3/1981 | Kotera et al. |
| 4,260,895 | A | 4/1981 | Schittenhelm |
| 4,260,898 | A | 4/1981 | Annis |
| 4,266,425 | A | 5/1981 | Allport |
| 4,267,446 | A | 5/1981 | Brown et al. |
| 4,274,005 | A | 6/1981 | Yamamura et al. |
| 4,292,538 | A | 9/1981 | Carlson |
| 4,317,037 | A | 2/1982 | Suzuki et al. |
| 4,366,382 | A | 12/1982 | Kotowski |
| 4,413,353 | A | 11/1983 | Macovski et al. |
| 4,425,426 | A | 1/1984 | Abbott et al. |
| 4,426,721 | A | 1/1984 | Wang |
| 4,445,226 | A | 4/1984 | Brody |
| 4,472,822 | A | 9/1984 | Swift |
| 4,511,799 | A | 4/1985 | Bjorkholm |
| 4,535,245 | A | 8/1985 | Zonneveld et al. |
| 4,578,803 | A | 3/1986 | Macovski |
| 4,578,808 | A | 3/1986 | West |
| 4,618,773 | A | 10/1986 | Drukier |
| 4,626,688 | A | 12/1986 | Barnes |
| 4,639,599 | A | 1/1987 | Ichihara |
| 4,670,892 | A | 6/1987 | Abele et al. |
| 4,855,598 | A | 8/1989 | Ohgoda et al. |
| 4,947,412 | A | 8/1990 | Mattson |
| 4,963,746 | A | 10/1990 | Morgan et al. |

OTHER PUBLICATIONS

MP Siedebend, et al, "Differential Energy Absorption X–Ray Cassette", *Journal of Applied Photographic Eng.,* (USA), vol. 3, No. 3, p. 162 (Summer 1977).

D.J. Drost, "Experimental Dual Xenon Detectors for Quantitative CT and Spectral Artifact Correction", *Medical Physics* (USA), vol. 7, No. 2, pp. 101–107 (Mar.–Apr. 1980).

Barnes, *Radiology,* vol. 156, pp. 537–540, 1985.

B.W. Gorski, "New Sensitomoetric Method", Proceedings of the Society of PhotoOptical Instrumentation Engineers, vol. 173. Application of Optical Instrumentation in Medicine VII, Toronto, Canada, Mar. 25–27, 1979 (Bellingham, WA, USA: Soc. Photo–Optical Instrumentation Engineers, 1979), pp. 28–32.

Alvarez, R.E., "Extraction of Energy Dependent Information in Radiography", PhD Dissertation, Dept. of Electrical Engineering, Stanford University, 1976.

Alvarez, R.E. and D. Cassell, "Film based digital x–rays: Using energy–selecting processing to substract unwanted materials", Diagnostic Imaging, vol. 5, No. 5, pp. 36–41, 1983.

Chan, J. L–H. "Some applications of filtered bremsstrahlung spectra in radiology", PhD Dissertation, Dept. of Electrical Engineering, Stanford University, 1980.

Yeh, P–S, "Selective material imaging using multiple energy measurements", PhD Dissertation, Dept. of Electrical Engineering, Stanford Univ., 1980.

Low, W., J. T. Steinberger, and E.A. Braun "The effect of alternating . . . ", Journal of the Optical Society of American, vol. 44, pp. 504–505., 1954, (Sep. 1976).

Adler, I., Gerald, J., Trombka, J., Schmadeback R., Lowman, P., Blodget H., Yin L., Eller E., Lamothe, R., Gorenstein, P., Bjorkholm P., Harris B., Gursky A., The Apollo 15 X–ray Flourescence Experiment, Proc. Third Lunar Sci. Conference, Grochim, Cosmo Chim Acta, Suppl. 3, vol. E., pp. 2157–2178 (1972).

D.R. Morgan, R.A. Sones, and G.T. Barnes, "Performance characteristics of a dual energy detector for digital scan projection radiography", *Medical Physics,* vol. 14, pp. 728–735, Sep./Oct. 1987.

Ergum, et al., Single Exposure Dual–Energy Computed Radiography: Improved Detection and Processing, *Radiology,* pp. 174, 243–249, 1990.

*Radiological Health Handbook,* Jan. 1970.

Barnes, Sones, Tesic, Morgan, Sanders, "Detector for Dual Energy Radiography", presented at 69th Scientific Assembly and Annual Meeting of Radiological Society of North America, Chicago, IL, Nov. 1983.

McCullough, E.C., "Photon Attenuation in Computed Tomography", *Med. Phys.,* vol. 2, pp. 307–320, 1975.

Richard A. Sones, et al, "Measured performance characteristics of a solid–state linear detector array", Med. Phys. 12(2), Mar./Apr. 1985, pp. 136–143.

I.T. Steinberger, et al, "Gudden–Pohl and Memory Effects in an Infra–Red Stimulated Phosphor", Dept. of Physics, the Hebrew Univ., J. Phys. Chem. Solids, Pergamon Press 1957, vol. 3, p. 133–140.

*Handbook of Chemistry and Physics,* 50th Ed. 1970, Chemical Rubber Co. R.C. Weast, Ed. pp. E–185–E196.

Hall, A.L. et al., "Experimental System for Dual Energy Scanned Projection Radiology", *Digital Radiology,* proc. of SPIE 314: 155–159, 1981.

Summer, F.G. et al., "Abdominal Dual Energy Imaging", *Digital Radiography,* proc. SPIE 314: 172–174, 1981.

Blank, N. et al: "Dual Energy Radiography: A Preliminary Study", *Digital Radiography,* proc. SPIE 314: 181–182, 1981.

Arnold, B.A. et al, "A Digital Radiography: An Overview", Proc. of SPIE, vol. 273, Mar. 1981.
Kruger, R.A. et al, "A Digital Video Image Processor for Real Time X–ray Subtraction Imaging", *Optical Engineering,* vol. 17, No. 6, 1978.
"Noise considerations in dual energy CT scanning", Kelcz, Joseph and Hilal, *Medical Physics,* vol. 6, No. 5, Sep./Oct. 1979, pp. 418–425.
"Energy–selective Reconstructions in X–ray Computerized Tomography", Robert E. Alvarez and Albert Macovski, Phys. Med. Biol., 1976, vol. 21, No. 5, 733–744.
"Split–Detector Computed Tomography: A Preliminary Report", Rodney A. Brooks, PhD., and Glovanni Di Chiro, M.D., Radiology, vol. 126, pp. 255–257, Jan., 1978.
"Time Delay and Integration Imager in GaAs", S. Chamberlain and R.F. Rutz, IBM Technical Disclosure Bulletin, vol. 23, No. 12, May 1981.
"Split Xenon Detector for Tomochemistry in Computed Tomography", Aaron Fenster, Journal of Computer Assisted Tomography, vol. 2, No. 3, 243–252, Jul. 1978.
"Hybrid Subtraction in Digital Fluorography", G.S. Keyes, S.J. Riederer, B.F. Belanger, W.R. Brody, SPIE, vol. 347 Application of Optical Instrumentation in Medicine X, 1982, pp. 34–41.
"Generalized Image Combinations in Dual KVP Digital Radiography", L.A. Lehmann, R.E. Alvarez, A. Macovski, and W.R. Brody, Medical Physics, vol. 8, No. 5, Sep./Oct. 1981, pp. 659–667.
"Design and Physical Characteristics of a Digital Chest Unit", R.A. Mattson, R.A. Sones, J.B. Stickney, M.M. Tesic, G.T. Barnes, SPIE, vol. 314 Digital Radiography, 1981, pp. 160–163.

"Absorption Edge Fluoroscopy Using Quasi–monoenergetic X–ray Beams", C.A. Mistretta, PhD, M.G. Ort, MS, F. Kelcz, MS, J.R. Cameron, PhD., .P. Siedband, MS and A.B. Crummy, MD, Investigative Radiology, vol. 8, Nov./Dec. 1973, pp. 402–412.

"Split–Filter Computed Tomography: A Simple Technique for Dual Energy Scanning", Brian Rutt and Aaron Fenster, J. Comput Assist Tomogr, vol. 4., No. 4, 1980, pp. 501–509.

"The Assessment of Bone Mineralization from the Relative Transmission of $^{241}$Am and $^{137}$Cs Radlations", G.W. Reed, First International Conference on Medical Physics, p. 174. (1966).

"The Effect of the kVp Level on EMI Values", Leslie M. Zatz, M.D., Radiology, vol. 119, Jun., 1976, pp. 683–688.

Jacobson, "Dichromatic Absorption Radiography: Dichromography", ACTA Radiologica, vol. 39, Jun. 1953, pp. 437–453.

* cited by examiner

SPLIT ENERGY LEVEL RADIATION DETECTION

Matter enclosed in heavy brackets [ ] appears in the original patent but forms no part of this reissue specification; matter printed in italics indicates the additions made by reissue.

DESCRIPTION

1. Technical Field

This invention relates to the field of medical diagnostic imaging and more particularly to an improved x-ray detector for use in digital radiography and fluoroscopy. The detector provides separate simultaneous representations of different energy radiation emergent from a subject.

2. Background Art

Radiography and fluoroscopy are long well known diagnostic imaging techniques.

In a conventional radiography system, an x-ray source is actuated to direct a divergent area beam of x-rays through a patient. A cassette containing an x-ray sensitive phosphor screen and film is positioned in the x-ray path on the side of the patient opposite the source. Radiation passing through the patient's body is attenuated in varying degrees in accordance with the various types of tissue through which the x-rays pass. The attenuated x-rays from the patient emerge in a pattern, and strike the phosphor screen, which in turn exposes the film. The x-ray film is processed to yield a visible image which can be interpreted by a radiologist as defining internal body structure and/or condition of the patient.

In conventional fluoroscopy, a continuous or rapidly pulsed area beam of x-rays is directed through the patient's body. An image intensifier tube is positioned in the path of the beam opposite the source with respect to the patient. The image intensifier tube receives the emergent radiation pattern from the patient, and converts it to a small, brightened visible image at an output face. Either a mirror or closed circuit television system views the output face and produces a dynamic real time visual image, such as on a CRT, a visual image for interpretation by a radiologist.

More recently, digital radiography and fluoroscopy techniques have been developed. In digital radiography, the source directs x-radiation through a patient's body to a detector in the beam path beyond the patient. The detector, by use of appropriate sensor means, responds to incident radiation to produce analog signals representing the sensed radiation image, which signals are converted to digital information and fed to a digital data processing unit. The data processing unit records, and/or processes and enhances the digital data. A display unit responds to the appropriate digital data representing the image to convert the digital information back into analog form and produce a visual display of the patient's internal body structure derived from the acquired image pattern of radiation emergent from the patient's body. The display system can be coupled directly to the digital data processing unit for substantially real time imaging, or can be fed stored digital data from digital storage means such as tapes or discs representing patient images from earlier studies.

Digital radiography includes radiographic techniques in which a thin fan beam of x-ray is used, and other techniques in which a more widely dispersed so-called "area beam" is used. In the former technique, often called "scan (or slit) projection radiography" (SPR) a fan beam of x-ray is directed through a patient's body. The fan is scanned across to the patient, or the patient is movably interposed between the fan beam x-ray source and an array of individual cellular detector segments which are aligned along an arcuate or linear path. Relative movement is effected between the source-detector arrangement and the patient's body, keeping the detector aligned with the beam, such that a large area of the patient's body is scanned by the fan beam of x-rays. Each of the detector segments produces analog signals indicating characteristics of the received x-rays.

These analog signals are digitized and fed to a data processing unit which operates on the data in a predetermined fashion to actuate display apparatus to produce a display image representing the internal structure and/or condition of the patient's body.

In use of the "area" beam, a divergent beam of x-ray is directed through the patient's body toward the input face of an image intensifier tube positioned opposite the patient with respect to the source. The tube output face is viewed by a television camera. The camera video signal is digitized, fed to a data processing unit, and subsequently converted to a tangible representation of the patient's internal body structure or condition.

One of the advantages of digital radiography and fluoroscopy is that the digital image information generated from the emergent radiation pattern incident on the detector can be processed, more easily than analog data, in various ways to enhance certain aspects of the image, to make the image more readily intelligible and to display a wider range of anatomical attenuation differences.

An important technique for enhancing a digitally represented image is called "subtraction". There are two types of subtraction techniques, one being "temporal" substraction, the other "energy" subtraction.

Temporal, sometimes called "mask mode" subtraction, is a technique that can be used to remove overlying and underlying structures from an image when the object of interest is enhanced by a radiopaque contrast agent, administered intra-arterially or intra-venously. Images are acquired with and without the contrast agent present and the data representing the former image is subtracted from the data representing the latter, substantially cancelling out all but the blood vessels or anatomical regions containing the contrast agent. Temporal subtraction is, theoretically, the optimum way to image the enhancement caused by an administered contrast agent. It "pulls" the affected regions out of an interfering background.

A principle limitation of digital temporal subtraction is the susceptibility to misregistration, or "motion" artifacts caused by patient movement between the acquisition of the images with and without the contrast agent.

Another disadvantage of temporal subtraction is that it requires the use of a contrast material and changes in the contrast caused by the agent must occur rapidly, to minimize the occurrence of motion caused artifacts by reducing the time between the first and second exposure acquisition. Temporal subtraction is also not useful in studies involving rapidly moving organs such as the heart. Also, the administration of contrast agents is contraindicated in some patients.

An alternative to temporal subtraction, which is less susceptible to motion artifacts, is energy subtraction Whereas temporal subtraction depends on changes in the contrast distribution with time, energy subtraction exploits energy-related differences in attenuation properties of various types of tissue, such as soft tissue and bone.

It is known that different tissues, such as soft tissue (which is mostly water) and bone, exhibit different characteristics in their capabilities to attenuate x-radiation of differing energy levels.

It is also known that the capability of soft tissue to attenuate x-radiation is less dependent on the x-ray's energy level than is the capability of bone to attenuate x-rays. Soft tissue shows less change in attenuation capability with respect to energy than does bone.

This phenomenon enables performance of energy subtraction. In practicing that technique, pulses of x-rays having alternating higher and lower energy levels are directed through the patient's body. When a lower energy pulse is so generated, the detector and associated digital processing unit cooperate to acquire and store a set of digital data representing the image produced in response to the lower energy pulse. A very short time later, when the higher energy pulse is produced, the detector and digital processing unit again similarly co-operate to acquire and store a set of digital information representing the image produced by the higher energy pulse. The values obtained representing the lower energy image are then subtracted from the values representing the higher energy image.

Since the attenuation of the lower energy x-rays by the soft tissue in the body is approximately the same as soft tissue attenuation of the higher energy x-rays, subtraction of the lower energy image data from the higher energy image data approximately cancels out the information describing the configuration of the soft tissue. When this information has been so cancelled, substantially all that remains in the image is the representation of bone. In this manner, the contrast and visibility of the bone is substantially enhanced by energy subtraction.

Energy subtraction has the advantage, relative to temporal subtraction, of being substantially not subject to motion artifacts resulting from the patient's movement between exposures. The time separating the lower and higher energy image acquisitions is quite short, often less than one sixtieth of a second.

Details of energy subtraction techniques in digital radiography and fluoroscopy are set forth in the following technical publications, all of which are hereby incorporated specifically by reference:

Hall, A.L. et al: "Experimental System for Dual Energy Scanned Projection Radiology". Digital Radiography proc. of the SPIE 314: 155–159, 1981;

Summer, F.G. et al: "Abdominal Dual Energy Imaging" Digital Radiography proc. SPIE 314: 172–174, 1981;

Blank, N. et al: "Dual Energy Radiography: a Preliminary Study". Digital Radiography proc. SPIE 314: 181–182, 1981; and Lehman, L.A. et al: "Generalized Image Combinations in Dual kVp Digital Radiography", Medical Physics 8: 659–667, 1981.

Dual energy subtraction has been accomplished, as noted above, by pulsing an x-ray source in a digital scanning slit device at two kVp's, typically 120 and 80 kVp, and sychronizing the pulses with a rotating filter which hardens the high kVp pulses by filtering out the lower energy x-ray. This results in the patient and x-ray detector sequentially seeing high energy and low energy beams from which the mass per unit area of bone and soft tissue can be solved for.

In energy subtraction, it is desirable that the two energy levels should be widely separated. This is necessary in order to accurately define the masses per unit area of bone and soft tissue.

With a slit scanning device, such as described above, sequentially pulsing the x-ray tube at 120 and 80 kVp is technically difficult and gives rise to very difficult problems in a practical clinical device. The switching frequency has to be on the order of 500 Hz. and insufficient photons (x-ray energy per pulse) results when the highest capacity x-ray tubes are combined with realistically narrow slit widths and scanning times.

In connection with CT (computerized tomography) applications, a two layer energy sensitive detector has been proposed. In this proposal, a first calcium fluoride layer is provided for sensing lower level x-ray radiation, and a second downstream sodium iodide layer senses higher energy radiation passing through the first layer. Light caused by radiation in each of the two layers is separately sensed by respective photomultiplier tubes.

DISCLOSURE OF THE INVENTION

The disadvantages and problems of the prior art are alleviated or eliminated by the use of an energy discriminating radiation detector including three elements. The detector includes a first element predominantly responsive to radiation of a first energy range, and a second element positioned behind the first, responsive to radiation in a second and higher energy range, along with a radiation filter interposed between the first and second elements.

Thus, an energy sensitive x-ray detector system for use in digital radiography is provided. For each picture element of the radiographic projection, the detector provides two readings from which the mass per unit area of bone and soft tissue through which the x-ray beam passes can be determined.

The energy sensitive x-ray detector employs a low atomic number phosphor screen or discrete array of phosphor segments coupled to a photodiode array, followed by a high atomic number of phosphor screen or discrete segment array similarly coupled.

An energy sensitive segment of an element of the detector system consists of a low atomic number phosphor coating layer coupled to a first photodiode, followed by a high atomic number phosphor coating layer coupled to a second photodiode. The low atomic number phosphor preferentially absorbs the low energy photons emerging from the patient and transmits most of the higher energy photons, a larger percentage of which are absorbed in the second (higher atomic number) phosphor.

Placing an appropriate filter between the two phosphor/photodiode arrays increases or hardens the effective energy of the x-ray spectrum incident on the second phosphor and results in a greater and more desirable energy separation between the x-ray spectra absorbed in the two phosphor layers.

In accordance with another embodiment, a split energy radiation detector is provided including a first energy responsive element comprising a quantity of phosphor material including one of yttrium oxysulfide and zinc cadmium sulfide, and a second energy responsive element positioned to receive energy passing through said first element, said second element including one of gadolinium oxysulfide and cadmium tungstate.

In accordance with another specific aspect of the invention, the radiation filter interposed between the two elements or layers is made of a material containing copper.

In accordance with a broader aspect of the invention, there is provided a split energy radiation detector screen comprising a deck of separate detector elements at least partially mutually superposed, each element being capable of producing information spatially locating radiation incident on the screen.

These and other aspects of the present invention will become more apparent from a consideration of the following description and of the drawings, in which:

BEST MODE FOR CARRYING OUT THE INVENTION

Figure 1:
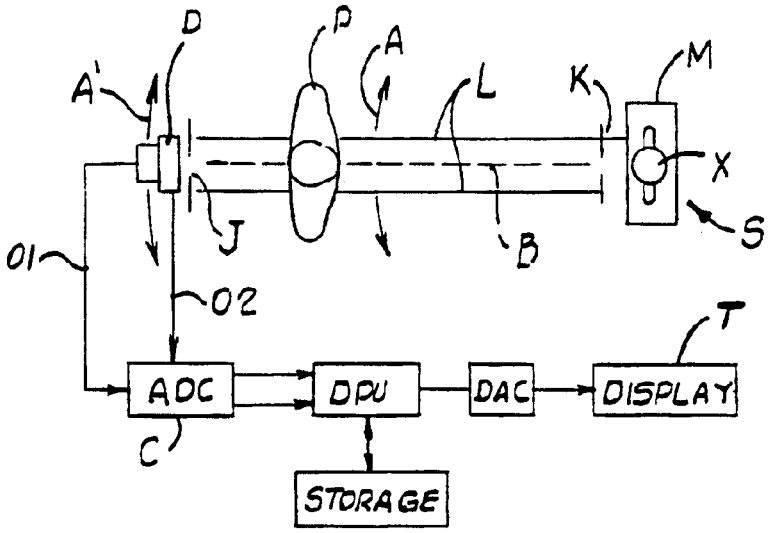
FIG. 1 is a plan pictoral and block illustration of a system incorporating the present invention.

FIG. 1 illustrates a slit projection type of digital radiography system in which the present invention is incorporated. The system S scans a thin fan beam of multi-energetic x-rays over a patient's chest and separately detects a pattern of x-rays of different energies emergent from the patient's body. Information represented by the detected x-rays is processed and displayed to illustrate a representation of an image of the patient's internal body structure or condition.

More specifically, the system S includes an x-ray source X affixed to mounting structure M for projecting a thin fan beam B of x-rays through the body of a patient P, to strike an aligned array D of detector segments. The fan beam B is confined by a forward slit K to substantially a vertical plane. The detector array D constitutes a vertical stack of individual detector segments E, described in more detail below, and aligned with the vertical plane defined by the beam B. An aft slit J attached to the detector D receives and aids in the definition of the planar beam B.

The x-ray source X is mounted on the structure M to rotate about a vertical axis, defined in FIG. 1 as extending into the paper. Mechanical linkage L couples the x-ray tube X to the detector array D and causes the detector array D to scan behind the patient's body in the directions of the arrows A, $A^1$, in order to maintain the detector D aligned with the beam B throughout the scanning rotative motion of the x-ray tube X.

The x-ray source X is controlled to emit either a continuous beam or a rapid succession of x-ray pulses in the form of the fan beam B. The x-ray tube X and the detector D are synchronously scanned, about a vertical axis, across the patient from one side of his body to the other. The detector output is periodically sampled. Each sampling produces signals representing a line of image information. Over the course of the scan from side to side, signals are developed describing a plurality of lines, which together constitute an area image of the patient's internal body structure.

Details of some aspects of a digital radiography system such as described above are set forth in the following publications, hereby expressly incorporated by reference.

Arnold, B.A. et al, "Digital Radiography: An Overview" Proc. of S.P.I.E. Vol. 273, Mar. 1981;

Kruger, R.A. et al, "A Digital Video Image Processor for Real Time X-Ray Subtraction Imaging" Optical Engineering Vol. 17 No. 6 (1978).

The detector D separately detects x-rays of different energy ranges impinging on the detector array. An element of the detector array, by way of two sets of leads 01, 02, transmits analog signals representing detected x-rays within lower and higher energy ranges, respectively.

The signals on the lead sets 01, 02, are provided to an analog-to-digital converter C which digitizes the outputs and feeds them to a digital processing and receiving unit DPU. The DPU processes these digitized output signals to construct a digital representation of an image of the patient's internal body structure scanned by the x-ray beam B, on a line-by-line basis. Digital signals from the DPU are converted to analog form by way of a digital-to-analog converter, and fed to a display unit T, which in response, produces an image in visual form corresponding to the image representing signals from the DPU.

Optionally, digital storage means can be provided in conjunction with the DPU in order to digitally store the image representations for future use. In such event, the digitally stored signals can be played black through the DPU, converted to analog form, and their corresponding images displayed at a later time on the display apparatus T.

Figure 1A:
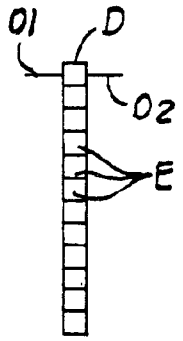
FIGS. 1A–1E are detail views illustrating a portion of the system of FIG. 1.
Figure 1B:
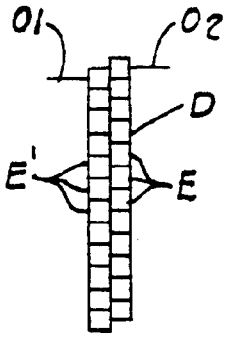

FIGS. 1A and 1B illustrate (in simplified form, for clarity) particular configurations of the face of the detector array D, as viewed from the right in FIG. 1. In FIG. 1A, for example, it is seen that the detector D comprises a linear vertically stacked elongated array of detector segments E.

An alternative embodiment to the vertical linear detector array shown in FIG. 1A is illustrated in FIG. 1B. This is known as a "staggered" array. The staggered array consists of two side-by-side vertical columns of detector segments E, $E^1$. One of the vertical columns, however, is slightly vertically displaced with respect to the other, by a distance equal to one-half the height of a single detector segment.

Figure 1C:
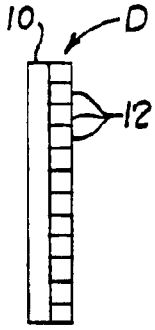
Figure 1D:
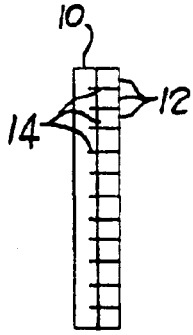
Figure 1E:
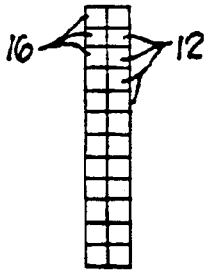

FIGS. 1C–1E illustrate in simplified form several embodiments of the detector configuration of FIG. 1A as viewed from the right side in FIG. 1A. FIGS. 1C–1E, however, are not intended to show the dual layered structure of the detector segments, which will be later discussed in detail, such as in connection with FIG. 2A. The detector arrays are divided into individual segments in one of three ways. In one embodiment, shown in FIG. 1C, the detector array D comprises an elongated vertical screen strip 10 of particles of radiation sensitive material which are glued together with a binder and affixed to a backing of a suitable material such as polyester. The radiation sensitive material respnds to incident radiation to produce light. Behind the radiation sensitive screen 10 is a vertical array of adjacent photodiodes 12. Each photodiode responds to radiation-caused light in the screen 10 to produce an analog electrical signal indicating brightness of the flash caused by the sensed radiation events. Each of the photodiodes 12 responds primarily to light from radiation events occurring within a portion of the screen material 10 located adjacent the photodiode.

Special "cellularized" detector configurations are illustrated in FIGS. 1D and 1E. Cellularized detectors have the advantage of reducing the effects of energy scatter within the detector array.

In the form illustrated in FIG. 1D, the detector screen 10 is grooved as illustrated for example at reference character 14, and the grooves are impregnated with a reflective material, such as aluminum oxide, to reduce the effects of light within the screen 10. The grooves are aligned with the junctions between each of the adjacent photodiodes 12.

Another form of cellularized detector arrangement is illustrated in FIG. 1E. In that embodiment, rather than utilizing an homogeneous screen, with or without grooves, separate crystalline portions 16 of radiation sensitive material are employed. Each crystal is matched to an adjoining photodiode and separated from adjacent crystals by a reflective layer. The size of each of the crystals corresponds to the size of its adjoining photodiode 12.

In all of the foregoing detector arrangements, the photodiodes are adhered to the screen portion 10 by a mechanical pressing operation, which can optionally be aided by a small quantity of adhesive, and/or a small amount of optical coupling grease to enhance the degree of optical coupling between the screen 10, or crystals 16, and the photodiodes 12.

As pointed out above, it is desirable, when practicing the energy subtraction image processing technique, to be able to separately represent different energy radiation which impinges on the detector segments. Herein is disclosed a particular dual layered, energy discriminating structure for each detector segment which facilitates achievement of this goal.

Figure 2:
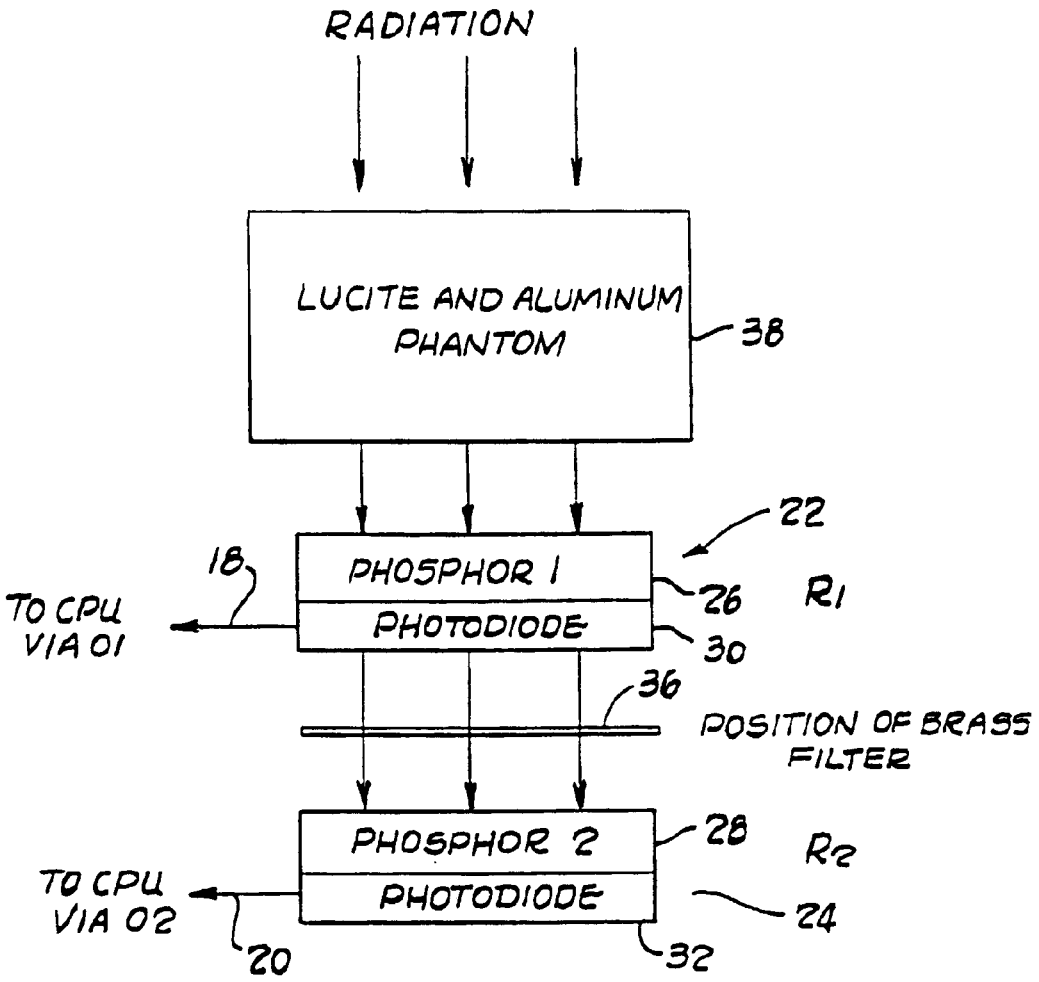
FIG. 2 is a side view illustrating a portion of the system illustrated in FIG. 1.

FIG. 2 illustrates a particular layered detector segment structure for use as a component of an energy sensitive radiation detector array D. The detector responds to radiation incident upon it, transmitted in a downward direction with respect to FIG. 2, to produce two outputs at leads 18, 20. The output at lead 18 represents radiation incident upon the detector segment having an energy level in a lower energy range. The output at the lead 20 represents the detector segment's response to incident x-ray radiation having an energy level in a second, higher energy range.

The detector segment includes a first elemental layer 22 primarily responsive to lower energy x-rays, and a second elemental layer 24 responsive to higher energy x-rays. Each of the layers 22, 24, includes a phosphor coating layer 26, 28, respectively, and a photodiode 30, 32, each respectively optically coupled to the phosphor layers 26, 28.

The choice of materials for the phosphor layers 26, 28, is significant. For example, preferred phosphor material for the first phosphor layer 26 include yttrium oxysulfide, and zinc cadmium sulfide. Alternative phosphors are barium sulfate, barium cadmium sulfate, lanthimum oxysulfide and barium fluorochloride.

For the second phosphor layer 28, preferred phosphors are gadolinium oxysulfide and cadmium tungstate. Alternative phosphor materials for the phosphor layer 28 include calcium tungstate and barium lead sulfate.

A preferred phosphor coating weight for the first phosphor layer 26 is about 20 to 100 milligrams (mg) per square centimeter ($cm^2$).

Preferred phosphor coating weights for the second phosphor layer lie in the range from approximately 50 to 1000 $mg/cm^2$.

The detector segment described above as embodying this invention is useful not only in linear detector element arrays such as used in scan or slit projection radiography, but also in larger area detector screens used in digital radiography systems incorporated divergent, "area" x-ray beams. In the latter case, a phosphor matrix embodying the detector can consist of either a single integral x-ray intensifying screen, a cellularized intensifying screen, or a cellularized matrix of individual phosphor crystals.

The segments have equal square dimensions in each layer.

The dimensions of the individual cell segments, where a cellularized structure is used, are equal to the photodiode matrix array spacing, such that each individual photodiode is congruent with its cell segment.

The cell segment dimensions are greater in the second layer of the detector than in the first. The relationship between cell segment dimensions in the first and second layers is expressed by the following:

$$(D2/D1)=(F2/F1)$$

where

Figure 3:
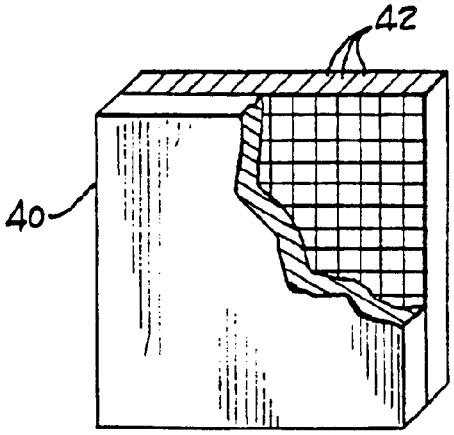
FIG. 3 is a perspective view of an alternate embodiment of a portion of the system of FIG. 1.
Figure 3A:
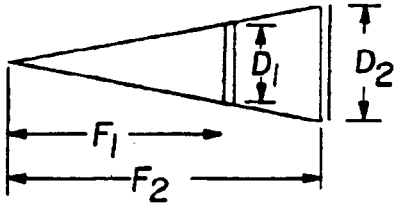
FIG. 3A is a graphical description of a preferred feature of the portion of the system illustrated in FIG. 2.

D2=the second detector photodiode, dimension;

D1=the first detector photodiode dimension;

F2=the distance from the x-ray source focal spot to the second detector layer 24, and F1=the distance from the x-ray focal spot to the first detector layer 22 (see FIG. 3A for a graphical illustration of these values).

This relation applies irrespective of whether a slit projection or area screen is employed.

It is desirable that the phosphor material selected for the first phosphor layer 26 have a primary absorber atomic number lying in the range of 39 to 57. The corresponding desirable atomic number range for the phosphor materials' primary absorber selected for the second layer 28 is 56 to 83.

The capability of the detector structure of this invention to distinguish between incident x-rays of differing energy ranges can be enhanced by the interposition of a filter layer 36 between the first and second layers 22, 24. A preferred filter material is one containing copper, such as brass. A preferred filter thickness, where brass is used, is approximately 0.5 millimeters (mm). The range of practical brass filter thicknesses is from about 0.2 mm to about 1.0 mm. Alternative filters can comprise either single or multiple filter elements made of material ranging in atomic number from approximately 24 to 58.

When a detector element constructed in accordance with the presently indicated preferred embodiment is used, a desirable energy spectrum for the x-ray source is from about 80 kVp to 150 kVp, or even higher, if tube technology permits.

The degree of spacing between the first and second layers 22, 24 of the detector segment is not particularly critical. Spacing between the first and second layers can suitably vary from almost physical contact to about 3 or more centimeters (cm). The spacing between the filter layer 36 and the first and second layers 22, 24 is not critical either.

As mentioned above, figures such as FIG. 1C show a side view of the detector array D in a form simplified for clarity. FIG. 1C is simplified in that it shows only one of the two detector elements or layers which each contain a plurality of detector segments as defined by the dimensions of the photodiodes 12.

Figure 2A:
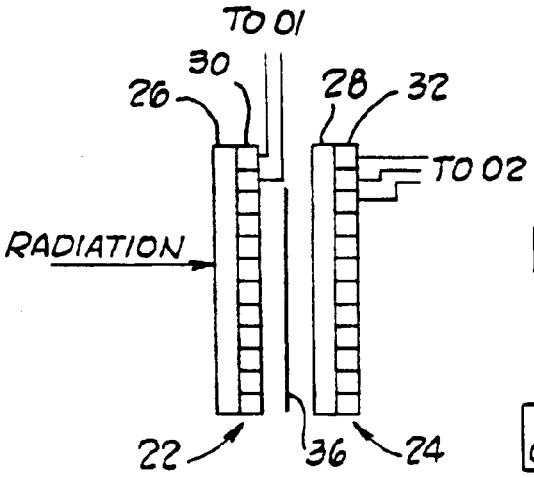
FIG. 2A is a detailed side view illustrating a portion of the system of FIG. 1.

FIG. 2A is provided to show the dual detector element (layer) structure which is the present subject. FIG. 2A shows how the detailed structure of FIG. 2 appears, when incorporated into a linear detector array D. FIG. 2A represents a side view of such an array.

FIG. 2A illustrates the two detector elements or layers 22, 24 one positioned behind the other with respect to the incident radiation from the source. Each element includes respectively a coating layer of phosphor 26, 28, and a set of photodiodes respectively indicated at 30, 32. Between the elements is located the filter element 36.

Each photodiode has a lead emergent therefrom for transmitting its analog radiation indicating signal to the appropriate one of the lead groups 01, 02, as described generally above. For purposes of clarity, only representative leads are shown in FIG. 2A.

The application of the split energy radiation detector of this invention is by no means limited to a linear array of detectors, for use in slit projection digital radiography, the environment described in detail above. The present invention can also be embodied in a so-called "area" detector, i.e., a relatively large rectangular radiation detector covering a relatively expansive portion of the patient's body, designed for use with so-called "area" beams, which diverge from the source to expose the radiation detector simultaneously over its entire face. One layer of such an area detector is illustrated in FIG. 3, it being understood that such an area detector includes two such layers, one behind the other.

Other types of area detectors exist in which use of this invention is advantageous. One such area detector includes a first phosphor layer of relatively low atomic number, as described above, coupled to a radiographic film layer, behind which is a second higher atomic number phosphor screen coupled to a second piece of film. Also, instead of the film portions, photoconductive or thermoluminescent plates could be used.

The principles analogous to the construction of the cellularized and uncellularized detectors described above in conjunction with FIGS. 1A through 1E can also be applied to area detectors as well.

Where such an area detector is used, the decoding electronics for locating the sites of radiation events across the face of an area detector are more complicated than in the case of the linear detector array discussed above. Details of a system for accomplishing this, which could analogously be applied to an area detector embodying this invention, are set forth in publication entitled "A Practical Gamma Ray Camera System Using High Purity Germanium" published in the February 1974 issue of IEEE Trans Nuc Sci and prepared by the Ohio State University Department of Nuclear Engineering under the auspices of a National Institute of Health contract. This publication is expressly incorporated by reference herein.

As may be implied by the above incorporated publication, the present invention is applicable to radiation detector technology employing other than phosphor materials which convert radiation events into light energy. The principles of this invention can be incorporated as well into radiation detection technology utilizing other types of radiation sensitive material, such as solid state materials which convert incident radiation into electrical signals which represent radiation incident on the material, without the need for converting such energy to the form of light.

Energy Sensitive Experiment and Results

Figure 4:
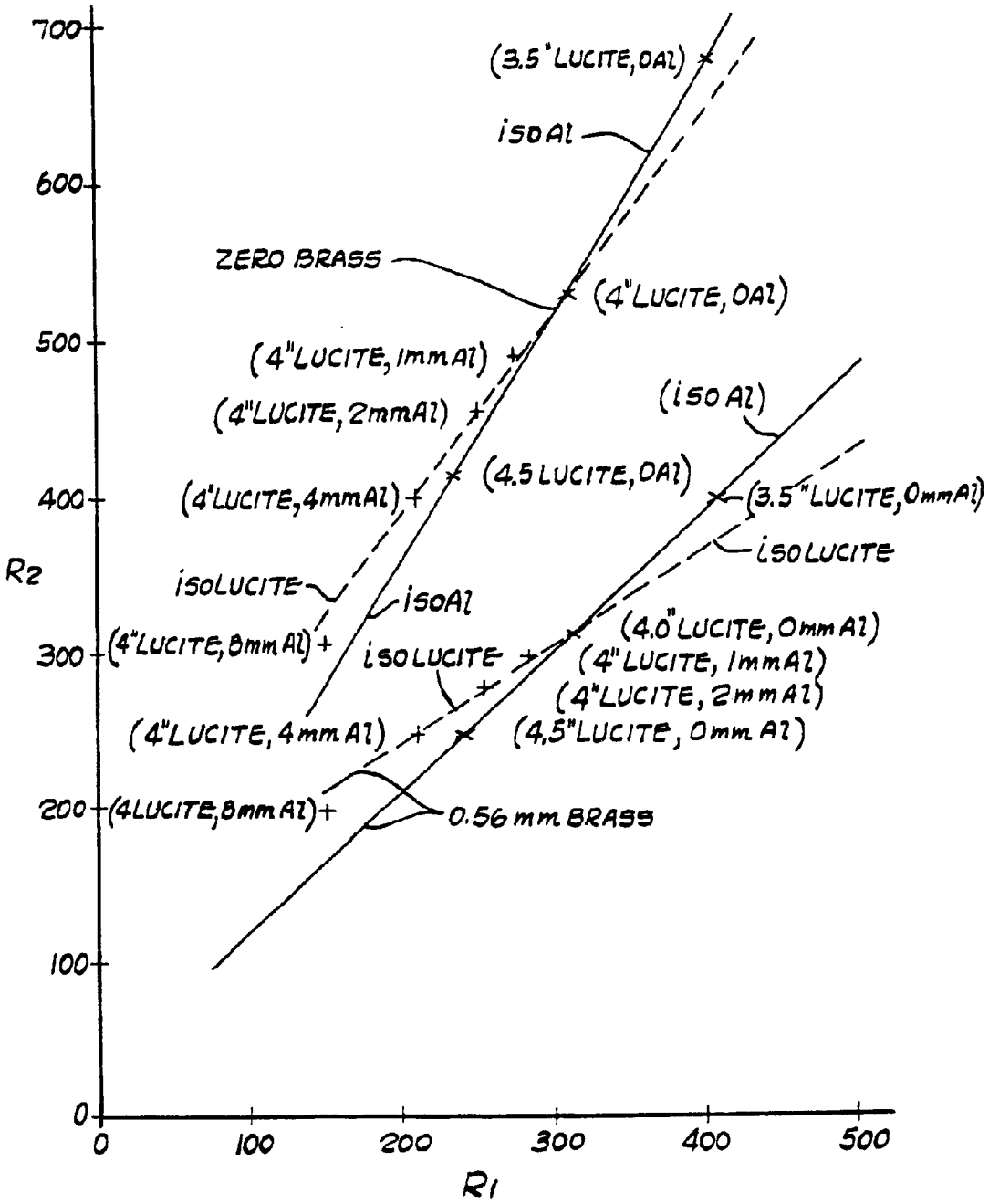
FIG. 4 is a graphical representation of operating characteristics of the portion of the system illustrated in FIG. 2.

The arrangement of the first and second detector layers employed in the experiment was in effect as shown in FIG. 2. A Lucite and aluminum phantom 38 was employed to simulate soft tissue and bone. The experimental results are tabulated in Table 1 for a typical 120 kVp radiation level and plotted in FIG. 4. Note how the iso-Lucite and iso-aluminum lines are more distinct when the brass filter is inserted between the first and second detector layers. From the data in Table 1 the relative uncertainty in estimating the thickness of Lucite and aluminum can be calculated and these results are tabulated in Table 2. Note that the ability to discriminate Lucite and aluminum is improved when the brass filter is inserted between the first and second detector.

The first phosphor layer was a 43 mg/cm$^2$ coating of yttrium oxysulfide. The second phosphor layer was a 110 mg/cm$^2$ coating of gadolinium oxysulfide.

TABLE 1

Experimental Results for a Constant, Typical Exposure Level

| Brass (cm) | Lucite (cm) | Aluminum (cm) | ($R_1$) | | ($R_2$) | |
|---|---|---|---|---|---|---|
| 0 | 0 | 0 | 3167 | | 3809 | |
| | 2.54 | 0 | 1662 | | 2466 | |
| | 5.08 | 0 | 917 | | 1451 | |
| | 8.89 | 0 | 398 | | 679 | |
| | 10.16 | 0 | 309 | 2.59 | 529 | 3.18 |
| | 11.43 | 0 | 235 | | 415 | |
| | 10.16 | .1 | 275 | | 491 | |
| | 10.16 | .2 | 249 | | 455 | |
| | 10.16 | .4 | 209 | 2.22 | 400 | 2.40 |
| | 10.16 | .8 | 150 | | 308 | |
| .0558 | 0 | 0 | 3196 | | 2293 | |
| | 2.54 | 0 | 1697 | | 1390 | |
| | 5.08 | 0 | 945 | | 338 | |
| | 8.89 | 0 | 408 | | 400 | |
| | 10.16 | 0 | 312 | 2.47 | 316 | 3.06 |
| | 11.43 | 0 | 242 | | 249 | |
| | 10.16 | .1 | 282 | | 298 | |
| | 10.16 | .2 | 255 | | 278 | |
| | 10.16 | .4 | 211 | 2.21 | 248 | 2.29 |
| | 10.16 | .8 | 154 | | 197 | |

TABLE 2

Lucite and Aluminum Discrimination for 10.2 cm of Lucite and 4 mm of aluminum

| Brass filter Thickness | Lucite Resolution | Aluminum Resolution | % Lucite Resolution | % Aluminum Resolution |
|---|---|---|---|---|
| 0 mm | 0.24 cm | 0.102 cm | 2.4 | 19.0 |
| 0.56 cm | 0.16 cm | 0.05 cm | 1.6 | 12.5 |

Figure 5:
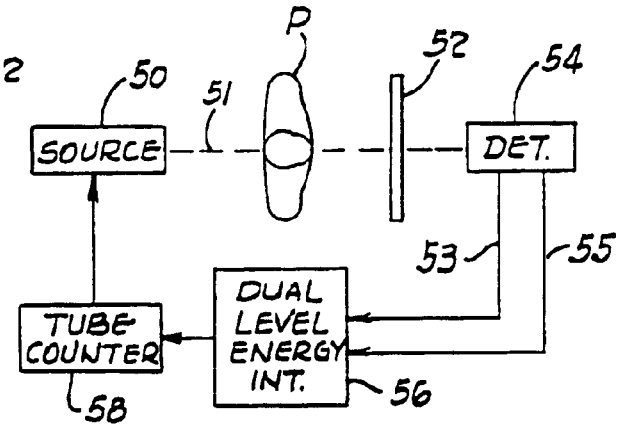
FIG. 5 is a block diagram illustrating another system incorporating an embodiment of the present invention.

A split energy level radiation detector such as illustrated in detail in FIG. 2 is also applicable in conventional radiography systems as a phototimer. FIG. 5 illustrates such a system. An x-ray source 50 directs a beam 51 of x-ray through the body of a patient P and onto a conventional radiation screen 52. A split level radiation detector 54, constructed in accordance with the structure detailed in FIG. 2 is positioned as a phototimer behind the screen to receive that portion of the x-ray energy from the beam 51 which passes through the screen 52.

The phototimer 54 produces, on leads 53, 55, signals indicating the amount of received energy in separate lower and higher energy ranges, respectively. These separate energy indicating signals are fed to a dual level energy integrator 56.

The energy integrator 56 includes circuitry for separately integrating the amount of energy, over time, indicated by the outputs on the leads 53, 55.

When the integrated energy values developed by the integrator 56 accumulate to a predetermined criteria, the integrator 56 produces a signal to a tube control circuit 58 which terminates operation of the source 50 in response to the accumulation of the particular predetermined integrated energy criterian.

The energy criterian governing the time of x-ray exposure can be selected in accordance with known principles by those with skill in the art. This criterion can be defined as the accumulation of a predetermined amount of energy in either of the sensed energy ranges, or can be a function of both sensed energy levels.

It is to be understood that this description of one embodiment of the present invention is intended as illustrative, and not exhaustive, of the invention. It is to be further understood that those of ordinary skill in the relevant art may make certain additions, deletions and modifications to this embodiment of the invention as described herein, without departing from the spirit or the scope of the invention, as described in the appended claims.

I claim:

1. [An] *In an imaging system, an* energy discriminating radiation detector comprising:

(a) a first element comprising a first material of a kind which is preferentially responsive to penetrative radiation of a first energy range;

(b) a second element comprising a second material different in kind from said first material and of a kind which is preferentially responsive to penetrative radiation of a second energy range extending higher than said first energy range and which is positioned to receive radiation which has penetrated through a portion of said first element; [and]

(c) a filter of penetrative radiation interposed between said first and second elements*; and*

(*d*) *means coupled to said elements for producing an image of a portion of an object from radiation emerging from the object and incident on the first and second elements*.

2. The detector of claim 1, wherein said filter contains copper.

3. The detector of claim 1, wherein said filter comprises brass.

4. The detector of claim 2 or 3, wherein said filter is selected to have a thickness of from about 0.2 mm to about 1.0 mm.

5. [The detector of claim 1,] *An energy discriminating radiation detector comprising:*

(*a*) *a first element comprising a first material of a kind which is preferentially responsive to penetrative radiation of a first energy range;*

(*b*) *a second element comprising a second material different in kind from said first material and of a kind which is preferentially responsive to penetrative radiation of a second energy range extending higher than said first energy range and which is positioned to receive radiation which has penetrated through a portion of said first element; and*

(*c*) *a filter of penetrative radiation interposed between said first and second elements;* wherein each said element comprises:

[(a)] a phosphor layer, and

[(b)] a photodiode optically coupled to the phosphor.

[6. A split energy radiation detector comprising:

(a) a first energy responsive element comprising a layer of phosphor material including one of yttrium oxysulfide and zinc cadmium sulfide; and (b) a second energy responsive element positioned to receive energy penetrating through said first element, said second element including a second phosphor layer comprising one of gadolinium oxysulfide and cadmium tungstate.]

[7. The detector of claim 6 further comprising:

a copper containing filter element interposed between said first and second elements.]

[8. The detector of claim 6, wherein:

(a) said first phosphor layer has a coating weight of about 20 to 100 mg/cm$^2$, and (b) said second phosphor layer has a coating weight of about 50 mg/cm$^2$ to 1000 mg/cm$^2$.]

[9. A digital radiography system comprising:

(a) an x-ray source for directing x-rays along a path;

(b) a split energy radiation detector spaced from the source to receive x-rays from said source, said detector comprising:

(i) a first element comprising a first material of a kind which is preferentially responsive to radiation of a first energy range and being located in said path;

(ii) a first sensor for sensing radiation response of said first element;

(iii) a second element at least partially positioned to receive source radiation passing through said first element, said second element comprising a second material of a kind which is preferentially responsive to radiation of a second energy level extending higher than said first range;

(iv) a second sensor for sensing radiation response of said second element; and (c) interpretive circuitry coupled to said sensors for at least partially digitizing information from said sensors and producing from said digitized information a representation of at least a portion of internal body structure of a subject when interposed in said path.]

10. The system of claim [9] *14*, wherein said first material includes one of yttrium oxysulfide and zinc cadmium sulfide.

11. The system of claim [9] *14*, wherein said second material includes one of gadolinium oxysulfide and calcium tungstate.

12. The system of claim [9] *14*, further comprising: an x-ray filter layer between said first and second elements.

13. The system of claim 12, wherein said filter layer contains copper.

14. [The system of claim 9,] *A digital radiography system comprising:*

(*a*) *an x-ray source for directing x-rays along a path;*

(*b*) *a split energy radiation detector spaced from the source to receive x-rays from said source, said detector comprising:*

(*i*) *a first element comprising a first material of a kind which is preferentially responsive to radiation of a first energy range and being located in said path;*

(*ii*) *a first sensor for sensing radiation response of said first element;*

(*iii*) *a second element at least partially positioned to receive source radiation passing through said first element, said second element comprising a second material of a kind which is preferentially responsive to radiation of a second energy level extending higher than said first range;*

(*iv*) *a second sensor for sensing radiation response of said second element; and*

(*c*) *interpretive circuitry coupled to said sensors for at least partially digitizing information from said sensors and producing from said digitized information a representation of at least a portion of internal body structure of a subject when interposed in said path;* wherein said sensors each comprise a photodiode.

15. [The system of claim 9,] *A digital radiography system comprising:*

(*a*) *an x-ray source for directing x-rays along a path;*

(*b*) *a split energy radiation detector spaced from the source to receive x-rays from said source, said detector comprising:*

(*i*) *a first element comprising a first material of a kind which is preferentially responsive to radiation of a first energy range and being located in said path;*

(*ii*) *a first sensor for sensing radiation response of said first element;*

(*iii*) *a second element at least partially positioned to receive source radiation passing through said first element, said second element comprising a second material of a kind which is preferentially responsive to radiation of a second energy range extending higher than said first range;*

(*iv*) *a second sensor for sensing radiation response of said second element; and*

(*c*) *interpretive circuitry coupled to said sensors for at least partially digitizing information from said sensors and producing from said digitized information a representation of at least a portion of internal body structure of a subject when interposed in said path;*

*wherein said sensors each comprise a photodiode; and* wherein said x-ray source is capable of simultaneously producing x-rays in both said energy ranges.

16. The system of claim [9] *14*, wherein each of said elements is substantially planar, one said element being substantially behind the other with respect to the source.

[17. An imaging method comprising the steps of:

(a) directing x-rays through a subject to be imaged, said x-rays including both higher and lower energy radiation;

(b) separately detecting higher and lower energy x-radiation emergent from the subject by passing said radiation successively through scintillators comprising respectively different kinds of materials each preferentially responsive to radiation of a different one of said lower and higher energy ranges, including sensing responses of said scintillators;

(c) at least partially digitizing information derived in said detecting step;

(d) processing said digitized information; and (e) utilizing said processed digital information to produce a representation of internal structure of the subject.]

[18. The method of claim 17, wherein said digital processing step includes a step of subtracting information obtained in said lower energy sensing step from information obtained in said higher energy sensing step.]

[19. The method of claim 17, wherein said sensing step comprises producing information in response to radiation incident on a plurality of separate detector elements, said information including spatial location representation of said incident radiation with respect to a said sensing element.]

20. [An] *In an imaging system, an* energy discriminating radiation detecting method utilizing first and second detector elements, a first of said elements being preferentially responsive to radiation of a first energy range, a second of said elements being preferentially responsive to [energy] *radiation* of a second *energy* range extending higher than said first energy range, said method comprising the steps of[;]*:*

(a) directing radiation extending over both said first and second energy ranges through a subject;

(b) positioning said first element to receive incident radiation emergent from the subject for response thereto;

(c) positioning said second element to receive radiation from the source passing through said first element, [and]

(d) filtering radiation transmitted through said first element prior to the arrival of said energy incident upon said second element*; and*

(*e*) *producing an image of a portion of the subject from the radiation emerging from the subject and incident on the first and second elements.*

21. A radiographic system comprising:

(a) an x-ray source;

(b) a radiation detector positioned to receive x-rays from the source;

(c) a phototimer comprising:

(i) an energy discriminating detector located to receive x-rays from the source and to produce signals indicating x-ray energy received in each of two energy ranges, and (ii) circuitry coupled between the discriminating detector and the source for controlling the source as a function of the x-rays detected in said two energy ranges.

22. A radiation imaging system comprising:

(a) a source of penetrative radiation;

(b) a dual energy detector assembly comprising two side-by-side columns of individual detector elements, one column being staggered with respect to the other by a distance equal to less than the dimension of a single detector element taken along the direction of its column, and additional detector elements positioned behind said columns, relative to said source;

(c) mounting structure for maintaining said source and said detector assembly sufficiently spaced to provide a subject examining space and for maintaining said detector aligned continuously in said penetrative radiation when produced by said source;

(d) power means for actuating said source to direct penetrative radiation through the subject examination space and incident onto the detector assembly;

(e) means coupled to said detector elements for producing an image of a portion of a subject, when located in the subject space, from radiation emergent from said subject.

23. The system of claim 22, wherein said staggered columns of detector elements are offset with respect to one another by a distance equal approximately one-half the height of a single detector element taken in a direction along its column.

24. An energy discriminating radiation detector comprising:

(a) a first component comprising a first material of a first kind which is preferentially responsive to penetrative radiation of a first energy range;

(b) a second component comprising a second material different in kind from said first material and of a kind which is preferentially responsive to penetrative radiation of a second energy range extending higher than said first energy range, said second component being positioned to receive radiation which has penetrated through a portion of said first component, and (c) means coupled to said first and second components to produce electrical signals representing radiation when incident respectively on said first and second components.

25. The detector of claim 24, [wherein: said filter comprises] *further comprising a filtering* material having an atomic number in the range of 24–58.

26. The detector of claim 24, wherein:

said first component comprises a phosphor layer comprising an element having an atomic number lying in the range of 39–57.

27. The detector of claim 24, wherein said second component comprises:

a phosphor layer comprising an element having an atomic number lying within the range of 56–83.

28. The detector of claim 24, wherein one of said first and second components comprises:

a phosphor layer proximate and aligned with a layer of light sensitive film.

29. The detector of claim [24] *1*, wherein one of said first and second [components] *elements* comprises:

a phosphor layer*; and*

*wherein said means for producing an image comprises a photoconductive plate, said phosphor layer being* proximate and aligned with a portion of *said* photoconductive plate.

30. The detector of claim [24] *1*, wherein one of said first and second [components] *elements* comprises:

a phosphor layer*; and*

*wherein said means for producing an image comprises a thermoluminescent plate, said phosphor layer being* proximate and aligned with a portion of *said* thermoluminescent plate.

31. The detector of claim 24, further comprising:

a filter of said penetrative radiation interposed between said first and second components.

32. The detector of claim 31, wherein:

said filter comprises material having an atomic number in the range of 24–58, and a thickness in the range of about 0.2 mm to 1.0 mm.

33. the detector of claim 24, wherein said second material comprises material having a primary radiation absorber having a higher atomic number than that of said first material.

34. The detector of claim 24, wherein:

(a) said first material comprises one of yttrium [oxysulfite] *oxysulfide*, zinc cadmium sulfide, barium sulfate, barium cadmium sulfate, [lanthium oxysulide] *lanthanum oxysulfide* and barium fluorochloride, (b) said second material comprises one of gadolinium oxysulfide, cadmium tungstate, calcium tungstate and barium lead sulfate.

35. The detector of claim 24, wherein:

(a) said first material comprises a first layer of phosphor material having a coating weight of about 20 to 100 $mg/cm^2$, and (b) said second material comprises a second phosphor layer having a coating weight of about 50 $mg/cm^2$ to 1000 $mg/cm^2$.

36. The detector of claim 24, wherein:

(a) said first component comprises a portion of a first scintillator material, and (b) said second component comprises a portion of a second scintillator material.

37. The detector of claim 24, further comprising:

a portion of penetrative radiation filtering material interposed between said first and second components and being capable of absorbing substantially all radiation incident on said filter element lying within said first energy range, while not absorbing substantially all such radiation of said second energy range.

38. A method for detecting area distribution of differing energy levels of penetrative radiation, said method comprising:

(a) detecting preferentially lower energy radiation by passing it through a first detector element including a scintillator and a plurality of segments;

(b) detecting higher energy radiation by transmitting radiation emergent from said first detector incident onto a second detector element including a scintillator and a plurality of segments;

(c) filtering penetrative radiation emergent from said first detector before said second detecting step, and (d) producing information in said first and second detecting steps spatially locating radiation over an area with respect to at least one of said detector elements.

39. An energy discriminating radiation detector comprising:

(a) a first component comprising a first phosphor material including a primary radiation absorber having an atomic number lying the range of 39–57;

(b) a second component comprising a second phosphor material aligned with said first phosphor material to receive radiation when said radiation has penetrated through a portion of said first component, said second phosphor material including a primary radiation absorber having an atomic number lying within the range of 56–83, and (c) means coupled to said first and second components for producing electrical signals representing radiation when incident on said detector.

40. An energy discriminating radiation detector comprising:

(a) a first component comprising a first material of a first kind which is preferentially responsive to penetrative radiation of a first energy range;

(b) a second component comprising a second material different in kind from said first material and of a kind which is responsive to penetrative radiation of a second energy range extending higher than said first energy range, said second component being aligned with said first component to receive radiation when said radiation has penetrated through a portion of said first component, and (c) means coupled to said first and second components to produce electrical signals representing penetrative radiation when incident on said detector.

41. A radiation imaging system comprising:

(a) a source for propagating penetrative radiation along a path from a focal spot;

(b) a detector assembly spaced from said source and interposed in said path, said detector assembly comprising:

(i) a front array of individual detector elements, each front array element including a penetrative radiation sensitive receiving face having a discrete geometry, said front array element faces being located at substantially a distance $F_1$ from said focal spot;

(ii) a rear array of individual detector elements, each said rear array element including a penetrative radiation sensitive receiving face having a discrete geometry, wherein each element of said rear array is substantially aligned behind a corresponding element of said front array, with respect to said focal spot, and in which each rear array element has a receiving face which has a larger area then the receiving face of its corresponding aligned front array element, said rear array receiving faces being located at substantially a distance $F_2$ from said focal spot, and (c) circuitry coupled to said detector arrays for producing a representation of radiation when incident on said detector elements.

42. The system of claim 41, wherein:

(a) said receiving faces of said detector elements of said front and rear arrays have similar geometry, and (b) a dimension $D_1$ of one of said front array elements is related to a corresponding dimension $D_2$ of one of said rear array elements by the following relation:

$$D_2/D_1=F_2/F_1.$$

* * * * *